United States Patent [19]

Kim et al.

[11] Patent Number: 5,094,108
[45] Date of Patent: Mar. 10, 1992

[54] ULTRASONIC CONTACT TRANSDUCER FOR POINT-FOCUSSING SURFACE WAVES

[75] Inventors: Byoung G. Kim; Se K. Lee; Jae O. Lee, all of Taejeon, Rep. of Korea

[73] Assignee: Korea Standards Research Institute, Taedok Science Town, Rep. of Korea

[21] Appl. No.: 589,768

[22] Filed: Sep. 28, 1990

[51] Int. Cl.$^5$ .................................. G01N 29/24
[52] U.S. Cl. ............................ 73/627; 73/629; 73/632; 310/335; 310/336
[58] Field of Search ............ 73/620, 627, 629, 632, 73/642; 310/335, 336

[56] References Cited

U.S. PATENT DOCUMENTS

| | | | |
|---|---|---|---|
| 2,912,854 | 11/1959 | Schubring | 73/627 |
| 3,299,695 | 1/1967 | Dickinson, III | 73/627 |
| 3,433,059 | 3/1969 | Cavalier | 310/336 |
| 4,475,054 | 10/1984 | Baumoel | 310/336 |

FOREIGN PATENT DOCUMENTS 0256847 10/1988 Japan ......................... 73/627

OTHER PUBLICATIONS

"Development of Surface Point-Focussing Ultrasonic Transducer Using PVDF", presented at IEEE 1989 Ultrasonics Symposium Proceedings, pp. 609-612, B. R. McAvoy, vol. 1, Nov. 16, 1989.
IEEE 1989 Ultrasonics Symposium and Short Courses, Program and Abstracts, p. 163, Legrand Hotel, Montreal, Quebec, Canada, Oct. 3-6, 1989.

Primary Examiner—Hezron E. Williams
Assistant Examiner—Rose M. Finley

[57] ABSTRACT

An ultrasonic contact transducer for point-focussing surface waves having a narrow beam width and a high sound intensity at a focal point in order to obtain better resolution and high beam intensity, which is applicable to the nondestructive testing technique of the surface or subsurface of a specimen to be tested, is disclosed. The ultrasonic contract transducer generates surface waves, focuses the waves at one point on the surface of the specimen and receives again the signals scattered from the surface flaws or subsurface flaws of the specimen, in order to detect the surface cracks, surface flaws, subsurface flaws of the specimen and to detect the delamination in a thin laminated film. The ultrasonic contact transducer comprises a curved piezoelectric element for generating ultrasonic waves, a acoustic contact lens to enable, in use, the ultrasonic waves generated by the curved piezoelectric element to be focussed at a flat surface of the specimen to enable the detection, sizing and imaging of surface cracks and subsurface detects of the specimen and to detect delamination in the laminated film specimen. The acoustic contact lens further includes a scattering means integrally formed to the acoustic contact lens to scatter the ultrasonic waves reflected from the flat bottom surface of the acoustic contact lens.

20 Claims, 3 Drawing Sheets

ULTRASONIC CONTACT TRANSDUCER FOR POINT-FOCUSSING SURFACE WAVES

BACKGROUND OF THE INVENTION

1. Field of the Invention

The present invention relates to an ultrasonic contact transducer for point-focussing surface waves, which is applicable to the nondestructive testing technique of the surface or subsurface of a specimen to be tested, and more particularly, to an ultrasonic contact transducer for generating surface waves, focussing the waves at one point on the surface of the specimen and receiving again the signals scattered from the surface flaws or subsurface flaws of the specimen, in order to detect the surface cracks, surface flaws, subsurface flaws of the specimen and to detect the delamination in a thin laminated film.

2. Information Disclosure Statement

Conventionally, in the ultrasonic testing of materials, focussed radiators have been frequently used to increase the sound intensity and to improve the resolution. The focussing has been realized by means of either curved radiators or plane radiators with curved contact lenses. However, so far, focussing contact type ultrasonic transducers have been designed in order to examine the interior of a specimen. Although a kind of, angle beam ultrasonic transducers have been designed and used to generate surface acoustic waves, they are not focussed but dispersed with a wide beam width resulting in poor resolution.

It is the object of the present invention to provide an ultrasonic transducer with a narrow beam width and a high sound intensity at the focal point on the surface of the specimen thereby improving flaw detection of the surface of the specimen.

The present invention, uses a curved piezoelectric element and an acoustic contact lens which enables the rays of the surface waves, such as Rayleigh waves, creeping longitudinal waves and horizontal shear surface waves, to be focussed at one point on the surface of the specimen to enhance flaw detection.

The narrow beam width at focal distance improves lateral resolution and more effectively sizes and images the surface flaws and subsurface flaws of the specimen relative to conventional angle beam transducers. Also, the high sound intensity at the focal distance enables the examination of the farther zone of the specimen possible. Furthermore, if creeping longitudinal waves are used, the transducer makes the examination of the dead zone in a specimen with an L or T type structure possible.

For further discussion of the present invention, see Kim et al, "Development of Surface Point-Focussing Ultrasonic Transducer Using PVDF", IEEE 1989 ULTRASONICS SYMPOSIUM PROCEEDINGS, PP. 609–612 B. R. MCAVOY. VOL 1, Nov. 16, 1989, and IEEE 1989 Ultrasonics Symposium and Short Courses, Program and Abstracts, page 163, Legrand Hotel, Montreal, Quebec, Canada, Oct. 3–6, 1989, both of which are incorporated herein by reference as if fully set forth hereat.

The preceding objects should be construed as merely presenting a few of the more pertinent features and applications of the invention. Many other beneficial results can be obtained by applying the disclosed invention in a different manner or modifying the invention within the scope of the disclosure. Accordingly, other objects and a fuller understanding of the invention may be had by referring to both the summary of the invention and the detailed description, below, which describe the preferred embodiment in addition to the scope of the invention defined by the claims considered in conjunction with the accompanying drawings.

SUMMARY OF THE INVENTION

The ultrasonic contact transducers for point-focussing of surface waves of the present invention is defined by the claims with a specific embodiment shown in the attached drawings. For the purpose of summarizing the invention, the invention relates to an ultrasonic contact transducer for generating, point-focussing and receiving surface acoustic waves having a narrow beam width and a high sound intensity at a focal point along a flat surface of a specimen for detecting, sizing and imaging of surface cracks and subsurface flaws therein and for detecting delamination in a laminated film specimen. The contact transducer comprises a curved piezoelectric element having a convex top surface and a concave bottom surface for generating ultrasonic waves. An acoustic contact lens is utilized in combination with the curved piezoelectric element. The acoustic contact lens has a top surface, an arced bottom edge, an exposed flat bottom surface and a convex front surface. The convex front surface of the acoustic contact lens contiguously receives the concave bottom surface of the curved piezoelectric element. This enables, in use, the ultrasonic waves generated by the curved piezoelectric element to be focussed at the flat surface of the specimen to enable the detection, sizing and imaging of surface cracks and subsurface flaws of the specimen and to detect delamination in the laminated film specimen.

Preferably, the acoustic contact lens of the ultrasonic contact transducer further includes a scattering means integrally formed on the top surface of the acoustic contact lens to scatter the ultrasonic waves reflected from the flat bottom surface of the acoustic contact lens.

Preferably, the acoustic contact lens of the ultrasonic contact transducer is of the shape of rotation body which is obtained by rotating a right-angled triangle with a critical angle about a rotation axis at the focal point, wherein the critical angle has a deviation from a predetermined value to optimize the generation of the surface acoustic waves, the rotation body has a predetermined rotation angle to meet the required beam intensity, the rotation axis is at a predetermined distance to meet the required focal distance, and the right-angled triangle has a predetermined size to meet the required beam intensity and to make the complete analysis of signal.

The ultrasonic contact transducer may be a single beam ultrasonic contact transducer or a double beam ultrasonic contact transducer. The single beam ultrasonic contact transducer uses a single acoustic contact lens with a curved piezoelectric element attached thereto, as described above.

A double beam ultrasonic contact transducer for generating, point-focussing and receiving surface acoustic waves having a narrow beam width and a high sound intensity at a focal point along a flat surface of a specimen for detecting, sizing and imaging of surface cracks and subsurface flaws therein and for detecting delamination in a laminated film specimen is also disclosed. The double beam ultrasonic contact transducer comprises a first and a second curved piezoelectric element with each element having a convex top surface and a concave bottom surface. A first and a second acoustic contact lens are employed with each contact lens having a top surface, an arced bottom edge, an exposed flat bottom surface and a convex front surface. Each convex front surface of each of the first and second acoustic contact lens contiguously receives each concave bottom surface of each of the curved piezoelectric element, respectively. A damper means is positioned between the first acoustic contact lens and the second acoustic contact lens for absorbing ultrasound waves thereby preventing ultrasound present in one of the first and second acoustic contact lens from interfering with the remaining acoustic contact lens, to enable the detection, sizing and imaging of surface cracks and subsurface defects of the specimen and to detect delamination in the laminated film specimen.

Preferably, each acoustic contact lens of the double beam ultrasonic contact transducer further includes a scattering means integrally formed on the top surface of each acoustic contact lens to scatter the ultrasonic waves reflected from the flat bottom surface of each acoustic contact lens.

Preferably, each acoustic contact lens of the double beam ultrasonic contact transducer is of the shape of rotation body which is obtained by rotating a right-angled triangle with a critical angle about a rotation axis at the focal point, said critical angle has a deviation from a predetermined value to optimize the generation of the surface acoustic waves, the rotation body has a predetermined rotation angle to meet the required beam intensity, the rotation axis is at a predetermined distance to meet the required focal distance, and the right-angled triangle has a predetermined size to meet the required beam intensity and to make the complete analysis of signal.

The more pertinent and important features of the present invention have been outlined above in order that the detailed description of the invention which follows will be better understood and that the present contribution to the art can be fully appreciated. Additional features of the invention described hereinafter form the subject of the claims of the invention. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

BRIEF DESCRIPTION OF THE DRAWINGS

For fuller understanding of the nature and objects of the invention, reference should be had to the following detailed description taken in conjunction with the accompanying drawings in which.

Similar reference characters refer to similar parts throughout the several views of the drawings.

DETAILED DESCRIPTION OF THE INVENTION

Figure 1A:
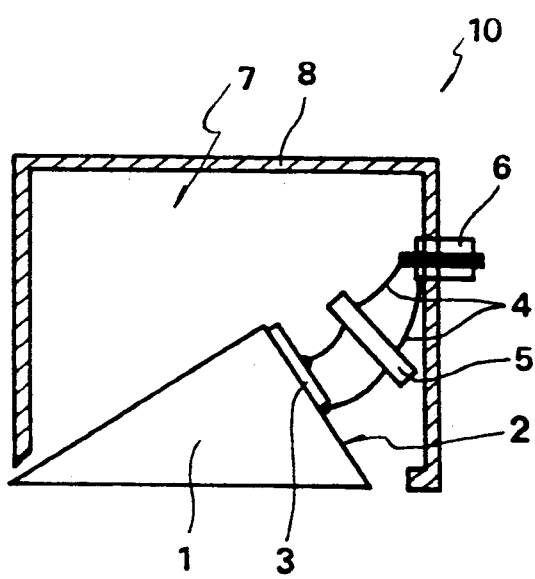
FIG. 1A is a schematic drawing showing the internal configuration of a conventional angle beam contact transducer to generate and receive surface ultrasonic waves.

FIG. 1A shows a schematic drawing of a conventional angle beam contact transducer 10 which consists of a wedge 1, such as for example, plexiglass, a piezoelectric element 3 attached to a flat top surface 2 of the wedge 1, lead wires 4, an electrical impedance matching part 5, electrical connector 6, backing 7 to mechanically damp the vibration of the piezoelectric element 3, and housing 8 for containing the required elements for the transducer mentioned above.

Figure 1B:
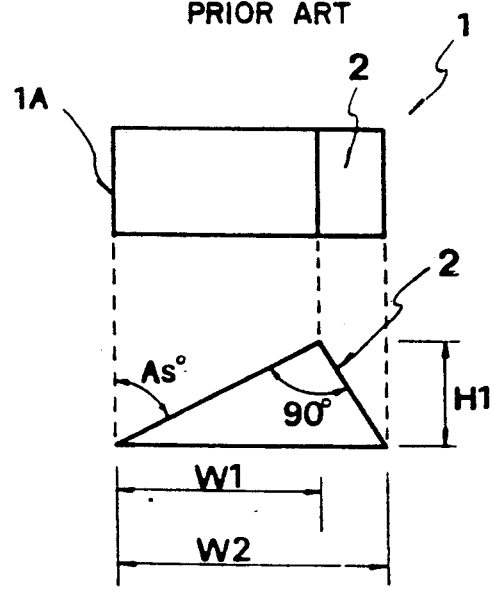
FIG. 1B is a drawing of the wedge in a conventional angle beam contact transducer to generate and receive surface ultrasonic waves.

FIG. 1B shows a drawing of the wedge 1 in a conventional angle beam transducer. The angle $As°$ of the wedge 1 is critical angle and is calculated using the equation for the generation of surface acoustic waves as follow:

$$Sin(As) = Ci/Cs \qquad (1)$$

where $Ci$ and $Cs$ are the sound velocities of incident waves in the lens and of surface acoustic waves on the surface of a test specimen, respectively. Incident waves can be longitudinal waves or shear waves. Generated surface acoustic waves can be Rayleigh waves, Creeping longitudinal waves or horizontal shear waves, and the like. Therefore, the incident angle, i.e. the wedge angle, depends on the type of incident wave and surface acoustic wave. Assuming that the sound velocity $Cs$ of Rayleigh wave is 2.97 km/s in steel as a test specimen and the sound velocity $Ci$ of longitudinal wave in plexiglass is 2.57 km/s, Rayleigh critical angle $As°$ is 59.9 degree. Also, in practical application, angle $As°$ may deviate from the value calculated by the equation (1) in order to optimize the generation of surface waves. It is important to note that the surface waves, generated with this conventional angle beam contact transducer, are not focused but are dispersed with a wide beam width resulting in poor resolution.

Figure 2A:
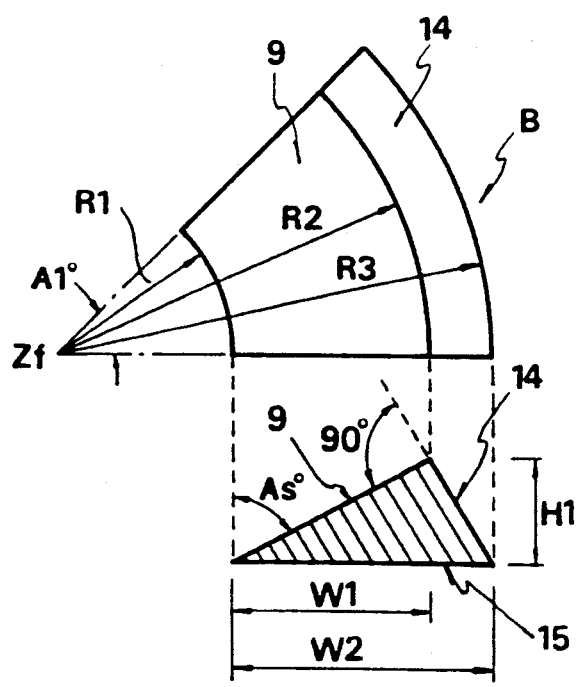
FIG. 2A is a drawing of contact type acoustic lens of the present invention.

FIG. 2A shows a drawing of a contact type of acoustic lens according to the present invention. The acoustic lens, hereinafter, is referred to as a basic lens "B", the structure of the basic lens "B" is described with the aid of FIG. 2B.

Figure 2B:
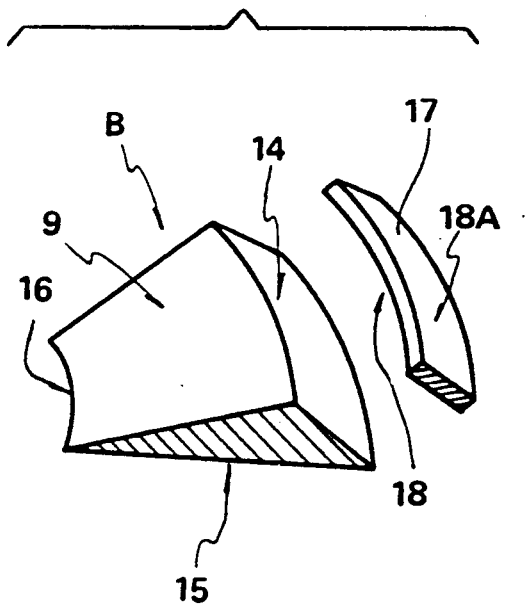
FIG. 2B is a three dimensional drawing of contact type acoustic lens and of piezoelectric element of the present invention.

FIG. 2B illustrates the three dimensional drawing of the acoustic lens and the curved piezoelectric element according to the present invention. As shown in the cross section of the basic lens "B", the vertical decline angle As° of a top surface 9 is a critical angle which is the same as the angle of the conventional angle beam transducer for generating the surface acoustic wave, and could have also some deviation from a predetermined value to optimize the generation of the surface acoustic waves. However, in order to focus the surface acoustic waves, the basic lens "B" has a flat bottom surface 15, an arced bottom edge 16 and a horizontally outward circular curved, i.e. convex, shaped front surface 14. The basic lens "B" in the present invention is of the shape of rotation body which can be constructed by rotating a right-angled triangle, with the critical angle As°, about a vertical axis at a focal point Zf. Wherein, the rotation body has a predetermined rotation angle to meet the required beam intensity, the rotation axis is at a predetermined distance from the arced bottom edge 16 of the basic lens "B" to meet the required focal distance, and the right-angled triangle to meet the required beam intensity and to make the complete analysis of signal. In contrast, the wedge 1 of the conventional angle beam transducer 10 has a straight line edge 1A and flat front surface 2, as illustrated in FIG. 1B.

The basic lens "B" has the minimum requirements to generate and focus surface acoustic waves. The angle A1°, which is 45 degrees in FIG. 2A, can be selected considering the required beam intensity and beam width of the focused surface acoustic waves. Also, the desired focal lengths of R1, R2 and R3, and the sizes of W1, W2 and the height H1 can be effectively selected to meet the requirements of the test purpose. The curved vibrator, i.e. a piezoelectric element 17, has a convex front surface 18A and a curved bottom surface, i.e. concave bottom surface 18, which is received on and attached to the curved front surface 14 of the basic lens "B". The thickness of the curved piezoelectric element 17 may be uniform or non-uniform, or the shape of that could be tapered. Also, its width, length and thickness should be selected properly to meet the requirements of the test purpose.

Figure 3A:
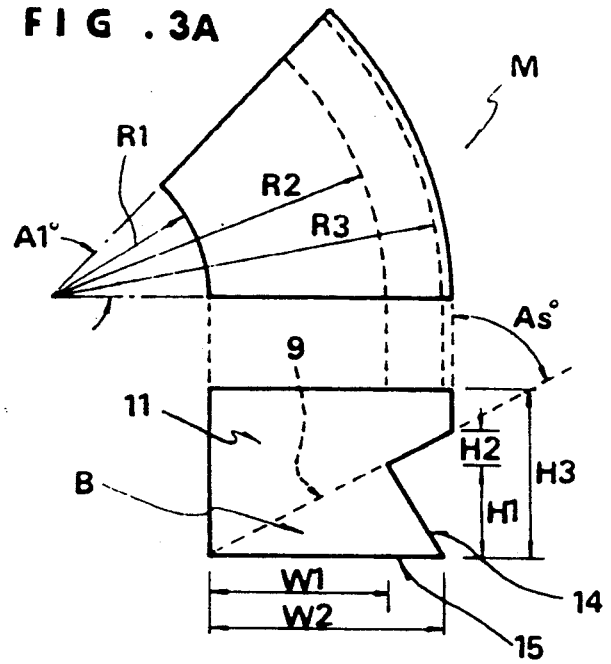
FIG. 3A is a drawing of another contact type acoustic lens of the present invention.

FIG. 3A shows a modified shape of the acoustic lens "B" according to the present invention. The modified lens, hereinafter, is referred to as "M". The principle involved and the design are the same as that of the basic lens "B", but modified only to form a scattering means 11 for scattering the ultrasonic waves reflected from the flat bottom surface 15 of the lens "B". The scattering means 11 is integrally formed on the front surface 9 of the basic lens "B". As in this modified lens "M", as long as the lens "B" has the basic features as presented in FIG. 2A and the flat bottom surface 15 is exposed, the modified acoustic lens "M" may be modified to an arbitrary shape. Further, the desired sizes of the heights H1, H2 and H3 can also be properly selected to meet the requirements mentioned above.

Figure 3B:
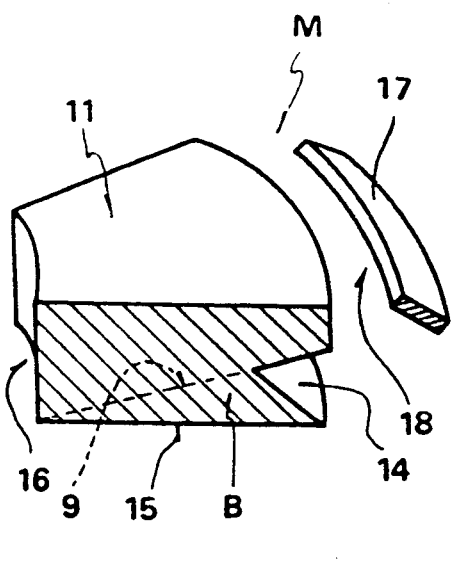
FIG. 3B is a three dimensional drawing of another contact type acoustic lens and of piezoelectric element of the present invention.

FIG. 3B shows a three dimensional drawing of the modified acoustic contact lens "M" and the curved piezoelectric element 17 according to the present invention. The curved piezoelectric element 17 will be attached on the curved front surface 14, as shown in FIG. 3B.

Figure 4:
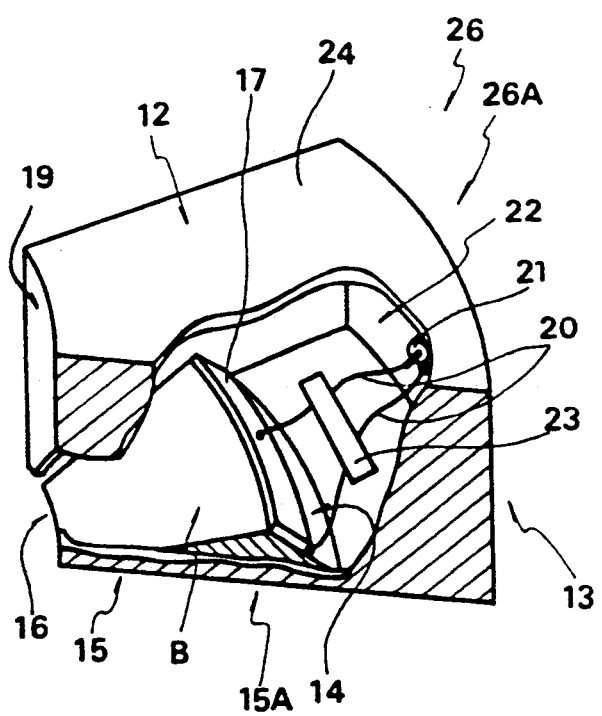
FIG. 4 is a three dimensional drawing of single beam ultrasonic transducer of the present invention.

FIG. 4 shows a three dimensional drawing of the single beam ultrasonic contact transducer according to the present invention. It consists of an acoustic lens "B" as shown in FIG. 2, the curved piezoelectric element 17 attached on the curved front surface 14 of the lens "B", lead wires 20, an electric connector 21, a backing 22 to mechanically damp the vibration of the piezoelectric element 17, an electrical impedance matching part 23 and the fan shape of housing 24. The housing 24 can be modified to any shape as long as the flat bottom surface 15 of the basic lens "B" is exposed. The housing 24 includes a flat front surface 12, a curved surface 13 and an opening 15A, a concave surface 19. The ultrasonic transducer 26 of the present invention which focuses surface waves and receives reflected waves is referred to as the acronym "SPFUT" (surface wave point focusing ultrasonic transducer). When a single beam SPFUT 26A is used, the generation of and reception of the surface waves is performed by an acoustic lens like that in FIG. 2 and a piezoelectric element 17. This type of transducer is used in the pulse-echo method.

Figure 5:
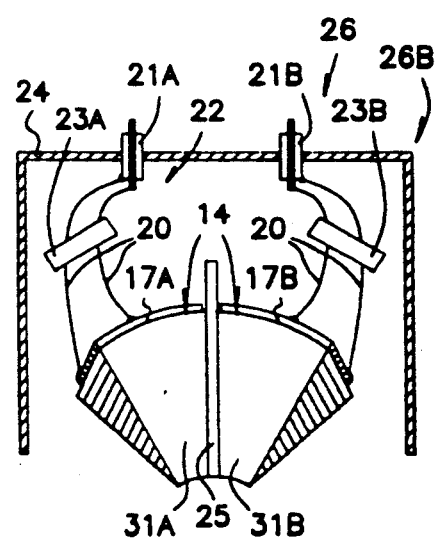
FIG. 5 is a schematic drawing of double beam ultrasonic transducer of the present invention.

FIG. 5 shows a schematic drawing of the double beam SPFUT 26B according to the present invention. The double beam SPFUT 26B consists of a pair of acoustic lenses "B", a first 31A and a second 31B acoustic lens, and a pair of curved piezoelectric elements, a first 17A and a second 17B piezoelectric element, respectively. Each piezoelectric element 17A and 17B is attached onto each of the curved front surface 14 of each lens "B". A damper 25 positioned between the first 31A and the second 31B acoustic lens absorbs ultrasound interfering between the two acoustic lenses 31A, 31B. The lead wires 20, a first 21A and a second 21B electric connector, backing 22 to mechanically damp the vibration of the piezoelectric elements 17A and 17B, a first 23A and second 23B electrical impedance matching part and housing 24 are also illustrated. In the dual beam SPFUT 26B the surface ultrasound generated from one acoustic lens is received by the other acoustic lens. This type of transducer is used in the pitch-catch method.

Figure 6:
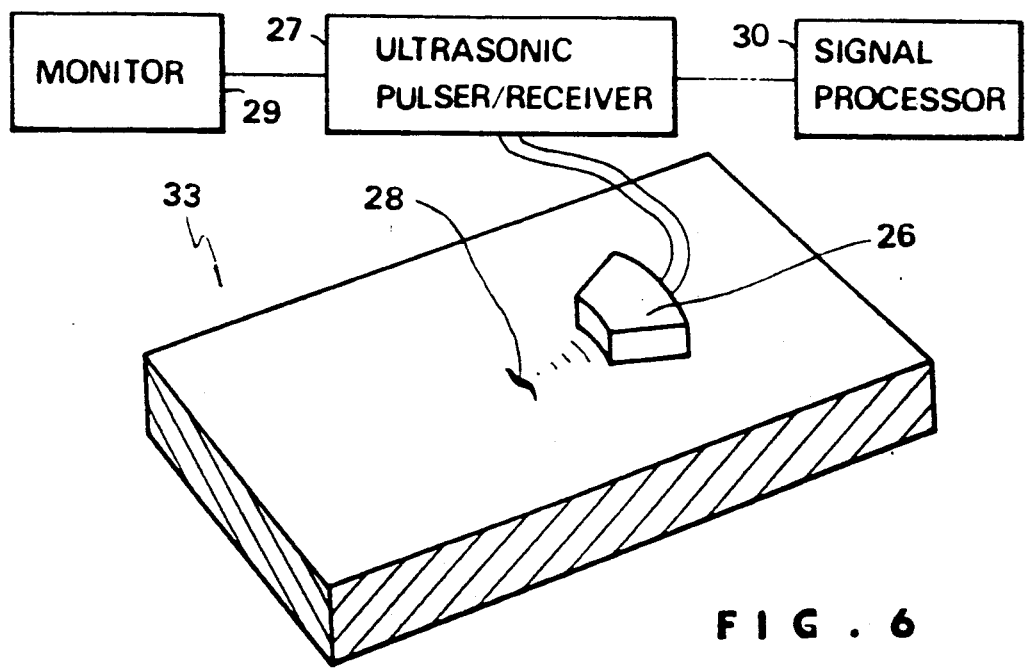
FIG. 6 is a schematic drawing of a nondestructive testing system using an ultrasonic transducer of the present invention.

FIG. 6 is a schematic drawing of the nondestructive testing system using SPFUT. The process to generate, focus and receive surface waves, and to analyze the received signals is as follows: First, longitudinal or shear waves are generated at the lens by driving the piezoelectric element, i.e. vibrator 17 using ultrasonic pulser 27. At this time, each ray of the waves generated on the curved front surface 14 of the basic lens "B" is perpendicular to the critical angle As°. Also, each ray of the waves generated on ne circular arc, parallel to flat bottom surface 15, in curved surface 14 has constant path length to the flat bottom surface 15. Thus, the rays form a circular arc with a width on the interface between the lens "B" and a specimen 33. Second, the incident longitudinal or shear waves, reaching to the interface, generate surface acoustic waves of circular arc shape. At this time, the surface acoustic waves generated at the circular arc in the interface have a constant phase and propagate to the center of the arced bottom edge 16. That is, all the generated surface acoustic waves are focused approximately at one point Zf, the center of the arced bottom edge 16. Third, the surface acoustic waves reflected and scattered from surface or subsurface flaws 28 are received by SPFUT 26. The signal is visualized and analyzed by a monitor 29 and a signal processor 30 through a ultrasonic pulser or/and receiver 27.

Figure 7:
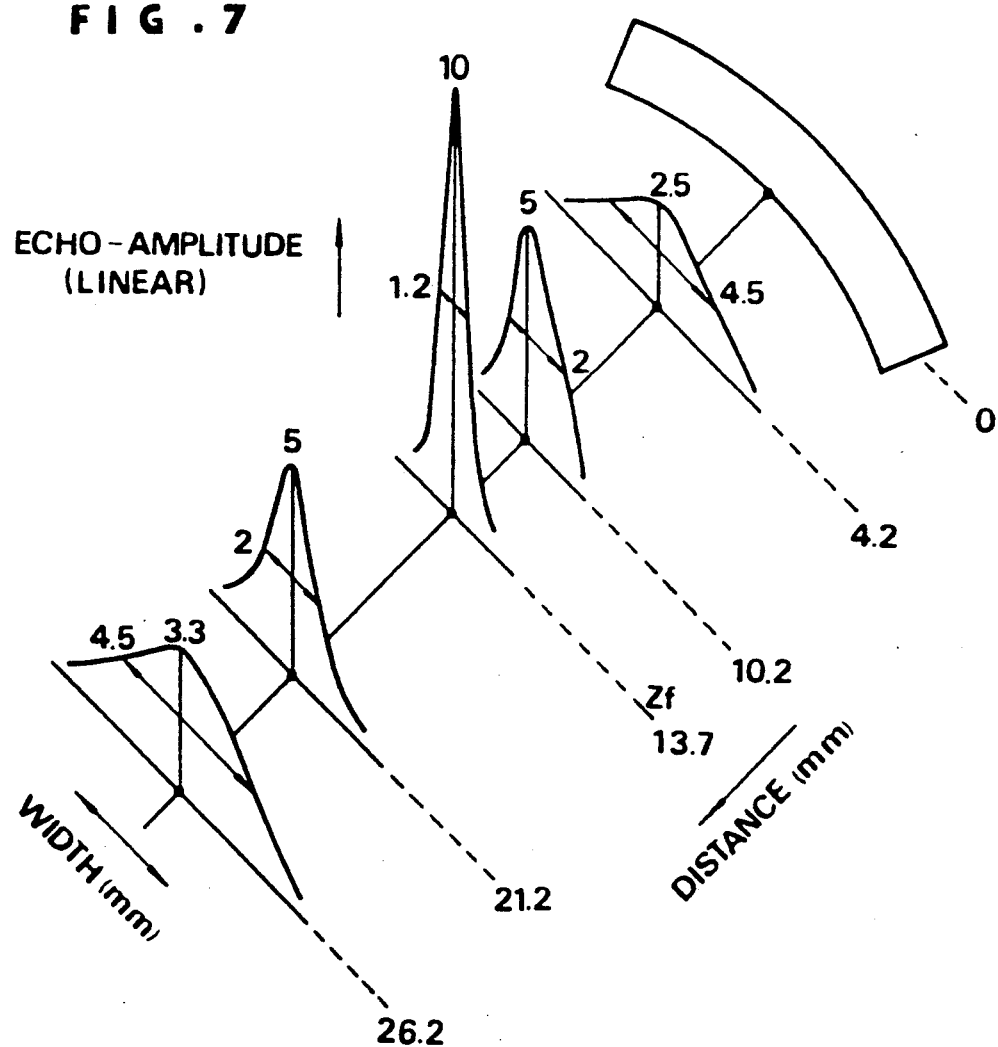
FIG. 7 is an example of beam profile shown by the examination of ultrasonic echo-amplitude for surface artificial flaw using an ultrasonic transducer of the present invention.

FIG. 7 shows the results of testing a steel block with a surface artificial flaw using a manufactured SPFUT for this experiment. The basic lens "B" of the single beam type of SPFUT 26A was designed such that the lengths R1, R2 and R3 are 15, 30, 35 mm, and the sizes W1 and W2 are 15 and 20 mm and the height H1 is 8.7 mm, the angle As° and A1° are 60 and 45, respectively.

At this time, focus waves were Rayleigh waves. Also the steel block with the surface artificial flaw of drill hole of 1 mm height and 1 mm diameter was used as a specimen. This result shows that the manufactured SPFUT 26A has the characteristic of high intensity and very narrow beam width of half width 1.2 mm at focal point Zf, as shown in the drawing.

From this experimental result it can be shown that the single beam and double beam SPFUT focus surface waves at one point effectively. With this feature enhanced sensitivity and resolution compared with conventional transducer are obtained. Therefore, the invention provides improved techniques for detecting and imaging surface cracks, surface flaws, subsurface flaws and the delamination of thin film, and also for the examination of a dead zone in a specimen with L or T type structure.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A single beam ultrasonic contact transducer for generating, point-focussing and receiving surface acoustic waves having a narrow beam width and a high sound intensity at a focal point along a flat surface of a specimen, said transducer comprising:
    a curved piezoelectric element 17 for generating ultrasonic waves and having a concave bottom surface 18 and a convex top surface 18A;
    an acoustic contact lens including a top surface 9 and an exposed flat bottom surface 15 with said lens top surface 9 and said lens flat bottom surface 15 converging to form an arced bottom edge 16; and
    said acoustic contact lens further including a convex front surface 14 opposite said arced bottom edge to contiguously receive said concave bottom surface 18 of said curved piezoelectric element 17 to enable, in use, said ultrasonic waves generated by said curved piezoelectric element 17 to be focussed at a flat surface of said specimen to enable detection, sizing and imaging of surface cracks and subsurface flaws of the specimen and to detect delamination in a laminated film specimen.

2. The single beam ultrasonic contact transducer of claim 1 wherein said acoustic contact lens further includes a scattering means integrally formed on said top surface of said acoustic contact lens to scatter said ultrasonic waves reflected from said flat bottom surface of said acoustic contact lens.

3. The single beam automatic contact transducer of claim 1 wherein said acoustic contact lens is of the shape of rotation body which is obtained by rotating a right-angled focal point spaced apart relative to said arced bottom edge of said acoustic contact lens.

4. The single beam ultrasonic contact transducer of claim 3 wherein said critical angle has a deviation from a predetermined value to optimize the generation of the surface acoustic waves.

5. The single beam ultrasonic contact transducer of claim 3 wherein said rotation body has a predetermined rotation angle to meet the required beam intensity.

6. The single beam ultrasonic contact transducer of claim 3 wherein said rotation axis is at a predetermined distance from said arced bottom edge of said acoustic contact lens to meet the required focal distance.

7. The single beam ultrasonic contact transducer of claim 3 wherein said right-angled triangle has a predetermined size to meet the required beam intensity and to make the complete analysis of signal.

8. The single beam ultrasonic contact transducer of claim 1 wherein said curved piezoelectric element has a predetermined thickness.

9. A single beam ultrasonic contact transducer for generating point-focussing and receiving surface acoustic waves having a narrow beam width and a high sound intensity at a focal point along a flat surface of a specimen, said transducer comprising:
    a curved piezoelectric element 17 for generating ultrasonic waves and having a concave bottom surface 18 and a convex top surface 18A;
    an acoustic contact lens including a top surface 9 and an exposed flat bottom surface 15 with said lens top surface and said lens flat bottom surface converging to form an arced bottom edge 16;
    said acoustic contact lens further including a convex front surface 14 opposite said arced bottom edge to contiguously receive said concave bottom surface 18 of said curved piezoelectric element 17 to enable, in use, said ultrasonic waves generated by said curved piezoelectric element 17 to be focussed at a flat surface of the specimen to enable detection, sizing and imaging of surface cracks and subsurface flaws of the specimen and to detect delamination in a laminated film specimen; and
    a scattering means integrally formed on said top surface of said acoustic contact lens for scattering said ultrasonic waves reflected from said flat bottom surface of said acoustic contact lens.

10. The single beam ultrasonic contact transducer of claim 9 wherein said acoustic contact lens is of the shape of rotation body which is obtained by rotating a right-angled triangle with a critical angle about a rotation axis at the focal point spaced apart relative to said arced bottom edge of said acoustic contact lens.

11. A double beam ultrasonic contact transducer for generating, point-focussing and receiving surface acoustic waves having a narrow beam width and a high sound intensity at a focal point along a flat surface of a specimen, said transducer comprising:
    a first and a second curved piezoelectric element with each element having a concave bottom surface and a convex top surface;
    a first and a second acoustic contact lens with each acoustic contact lens including a top surface 9 and an exposed flat bottom surface 15 with said lens top surface and said lens exposed flat bottom surface converging to form an arced bottom edge 16;
    each said acoustic contact lens further including a convex front surface 14 opposite said arced bottom edge to contiguously receive said concave bottom surface 18 of said curved piezoelectric element 17 to enable, in use, said ultrasonic waves generated by said curved piezoelectric element 17 to be focussed at a flat surface of the specimen, respectively; and
    a damper means positioned between said first acoustic contact lens and said second acoustic contact lens for absorbing ultrasound waves thereby preventing ultrasound present in one of said first and second acoustic contact lens from interfering with the remaining said acoustic contact lens to enable the detection, sizing and imaging of surface cracks and subsurface flaws of the specimen and to detect delamination of the laminated film specimen.

12. The double beam ultrasonic contact transducer of claim 11 wherein each said acoustic contact lens further includes scattering means integrally formed on said front surface of each said acoustic contact lens to scatter said ultrasonic waves reflected from said flat bottom surface of each said acoustic contact lens.

13. The double beam ultrasonic contact transducer of claim 11 wherein each said acoustic contact lens is of the shape of rotation body which is obtained by rotating a right-angled triangle with a critical angle about a rotation axis at the focal point spaced apart relative to said arced bottom edge of each said acoustic contact lens.

14. The double beam ultrasonic contact transducer of claim 13 wherein said critical angle has a deviation from a predetermined value to optimize the generation of the surface acoustic waves.

15. The double beam ultrasonic contact transducer of claim 13 wherein said rotation body has a predetermined rotation angle to meet the required beam intensity.

16. The double beam ultrasonic contact transducer of claim 13 wherein said rotation axis is at a predetermined distance from said arced bottom edge of each said acoustic contact lens to meet the required focal distance.

17. The double beam ultrasonic contact transducer of claim 13 wherein said right-angled triangle has a predetermined size to meet the required beam intensity and to make the complete analysis of signal 18. The double beam ultrasonic contact transducer of claim 11 wherein each said curved piezoelectric element has a predetermined thickness.

19. A double beam ultrasonic contact transducer for generating, point-focussing and receiving surface acoustic waves having a narrow beam width and a high sound intensity at a focal point along a flat surface of a specimen, said transducer comprising:

a first and a second curved piezoelectric element with each element having a convex top surface and a concave bottom surface;

a first and a second acoustic contact lens with each acoustic contact lens including a top surface 9 and an exposed flat bottom surface 15 with said lens top surface and said lens exposed flat bottom surface converging to form an arced bottom edge 16;

each said acoustic contact lens further including a convex front surface 14 opposite said arced bottom edge to contiguously receive said concave bottom surface 18 of said curved piezoelectric element 17 to enable, in use, said ultrasonic waves generated by said curved piezoelectric element 17 to be focussed at a flat surface of the specimen, respectively;

scattering means formed on said top surface of each said acoustic contact lens for scattering said ultrasonic waves reflected from said flat bottom surface of each said acoustic contact lens; and a damper means positioned between said first acoustic contact lens and said second acoustic contact lens for absorbing ultrasound waves thereby preventing ultrasound present in one of said first and second acoustic contact lens to enable the detection, sizing and imaging of surface cracks and subsurface flaws of the specimen and to detect delamination in the laminated film specimen.

20. The double beam ultrasonic contact transducer of claim 19 wherein each said acoustic contact lens is of the shape of rotation body which is obtained by rotating a right-angled triangle with a critical angle about a rotation axis at the focal point spaced apart relative to said arced bottom edge of each said acoustic contact lens.

* * * * *

UNITED STATES PATENT AND TRADEMARK OFFICE
CERTIFICATE OF CORRECTION

PATENT NO. : 5,094,108

DATED : March 10, 1992

INVENTOR(S) : Kim et al.

It is certified that error appears in the above-identified patent and that said Letters Patent is hereby corrected as shown below:

Column 5, line 32; "front" should read --top--.

Column 5, line 48; "front" should read --top--.

Column 6, line 5; "front" should read --top--.

Column 6, line 43; insert --curved front surface 14 and has a constant incident angle,-- after the word "the".

Column 6, line 44; "ne" should read --one--.

Column 6, line 45; insert --front-- after the word "curved".

Column 7, line 55; "automatic" should read --ultrasonic--.

Column 7, line 58; insert --triangle with a critical angle about a rotation axis at the-- after the word "right-angled".

UNITED STATES PATENT AND TRADEMARK OFFICE
CERTIFICATE OF CORRECTION

PATENT NO. : 5,094,108

DATED : March 10, 1992

INVENTOR(S) : Kim et al.

It is certified that error appears in the above-indentified patent and that said Letters Patent is hereby corrected as shown below:

Column 9, line 7; "front" should read --top--.

Signed and Sealed this

Twenty-eighth Day of September, 1993

Attest:

BRUCE LEHMAN

Attesting Officer

Commissioner of Patents and Trademarks